US 6,456,890 B2

(12) United States Patent
Pianca et al.

(10) Patent No.: US 6,456,890 B2
(45) Date of Patent: Sep. 24, 2002

(54) LEAD WITH POLYMERIC TUBULAR LINER FOR GUIDEWIRE AND STYLET INSERTION

(75) Inventors: Anne M. Pianca, Valencia; Gene A. Bornzin, Simi Valley; Christopher R. Jenney, Valencia; Kevin L. Morgan, Simi Valley; Sheldon Williams, Green Valley, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/797,531

(22) Filed: Feb. 28, 2001

Related U.S. Application Data
(60) Provisional application No. 60/204,297, filed on May 15, 2000.

(51) Int. Cl.[7] .................................................. A61N 1/00
(52) U.S. Cl. ........................................................ 607/122
(58) Field of Search ........................... 607/116, 122–128

(56) References Cited

U.S. PATENT DOCUMENTS

| | | | |
|---|---|---|---|
| 5,246,014 A | 9/1993 | Williams et al. ............ 607/122 |
| 5,324,321 A | * 6/1994 | Pohndorf et al. | |
| 5,425,755 A | 6/1995 | Doan ........................ 607/119 |
| 5,439,485 A | 8/1995 | Mar et al. .................. 607/119 |
| 5,456,707 A | 10/1995 | Giele ........................ 607/127 |
| 5,476,495 A | 12/1995 | Kordis et al. ............. 607/122 |
| 5,609,151 A | 3/1997 | Mulier et al. ............. 128/642 |
| 5,609,622 A | 3/1997 | Soukup et al. ............. 607/122 |
| 5,643,255 A | 7/1997 | Organ ........................ 606/41 |
| 5,674,272 A | 10/1997 | Bush et al. ................. 607/122 |
| 5,676,694 A | 10/1997 | Boser et al. ............... 607/122 |
| 5,683,444 A | 11/1997 | Huntley et al. ............ 607/122 |
| 5,755,766 A | 5/1998 | Chastain et al. ........... 607/122 |
| 5,796,044 A | 8/1998 | Cobian et al. ............. 174/103 |
| 5,803,083 A | 9/1998 | Buck et al. ............. 128/660.03 |
| 5,803,928 A | 9/1998 | Tockman et al. .......... 607/122 |
| 5,820,594 A | 10/1998 | Fontirroche et al. ........ 604/96 |
| 5,897,529 A | 4/1999 | Ponzi ......................... 604/95 |
| 5,897,585 A | 4/1999 | Williams .................... 607/122 |
| 5,906,605 A | 5/1999 | Coxum ....................... 604/525 |
| 5,938,694 A | 8/1999 | Jaraczewski et al. ....... 607/122 |
| 5,957,842 A | * 9/1999 | Littmann et al. | |
| 6,004,310 A | 12/1999 | Bardsley et al. ........... 604/524 |
| 6,129,749 A | * 10/2000 | Bartig et al. | |
| 6,321,102 B1 | * 11/2001 | Spehr et al. | |

* cited by examiner

Primary Examiner—Mark Bockelman

(57) ABSTRACT

An implantable lead for electrical stimulation of the body includes an elongated multi-lumen tube with a distal tip electrode having a longitudinally extending central bore. A cable conductor is received in one lumen of the multi-lumen tube for electrical connection to the tip electrode and an elongated polymeric tubular liner having a coefficient of friction in the range of 0.01 to 0.20 is received in another lumen of the multi-lumen tube generally aligned with the bore of the distal tip electrode for freely receiving a guidewire through the tubular liner and through the bore of the distal tip electrode. An electrically conductive proximal pin is attached to the multi-lumen tubing distant from the tip electrode and, in one embodiment, the cable conductor and the proximal end of the polymeric tubular liner are attached to the proximal pin. Initially, the guidewire is implanted into the body along a desired trajectory. With the polymeric tubular liner inserted, first the distal tip electrode, then the remainder of the multi-lumen tube, are slid onto the guidewire such that the guidewire slidably advances within the polymeric tubular liner. Thereupon, the multi-lumen tube is advanced along the guidewire until a desired site is achieved and the guidewire is removed from the body and the multi-lumen tube. In another embodiment, the distal tip electrode has no central bore but the elongated polymeric tubular liner is axially aligned with the distal tip electrode for freely receiving a stylet which is attached with the distal tip electrode.

8 Claims, 7 Drawing Sheets

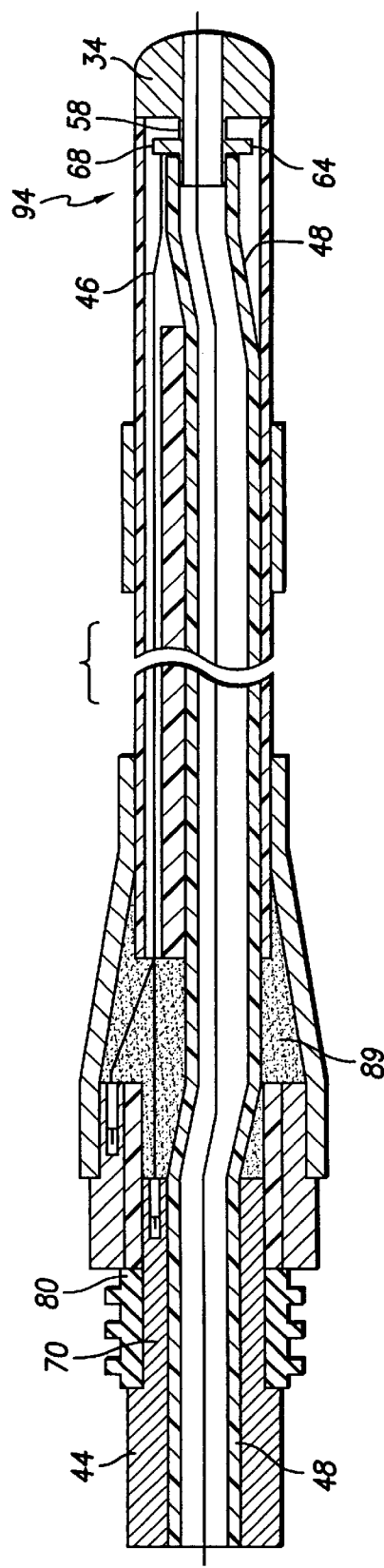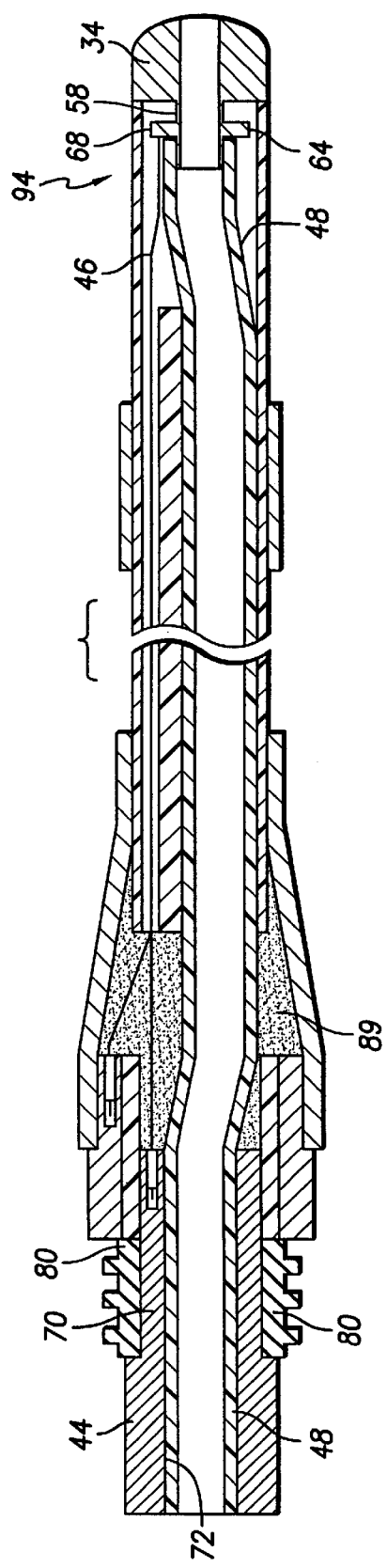

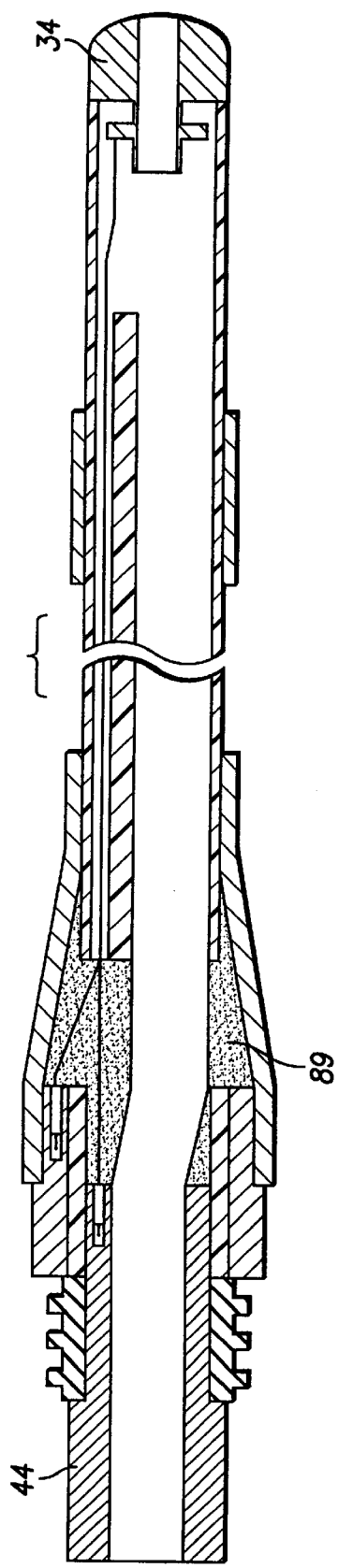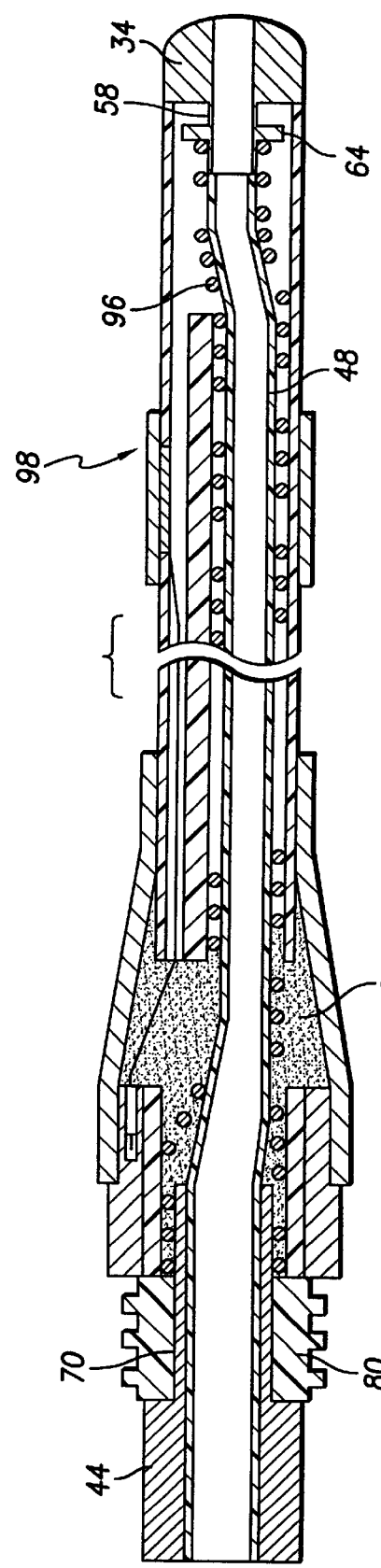

LEAD WITH POLYMERIC TUBULAR LINER FOR GUIDEWIRE AND STYLET INSERTION

This application claims benefit of provisional application Ser. No. 60/204,297 filed on May 15, 2000.

FIELD OF THE INVENTION

The present invention relates generally to implantable medical devices for providing stimulating pulses to selected body tissue, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled conductor surrounded by an insulating tube or sheath typically couples the connector pin at the proximal end and the electrode at the distal end.

With the onset of multi chamber pacing for Congestive Heart Failure (CHF), there has been much discussion and debate in the medical community as to what is the most desirable lead possible for left ventricular (LV) stimulation. The overwhelming opinion of physicians seems to be that the "best" LV lead is the one that is easiest to place and involves the fewest procedures and parts. As a result of recent advancements in techniques and instrumentation, many physicians have become convinced that a lead that is placed with a guidewire, instead of a stylet, is superior.

Investigations have been performed on an LV lead that can be placed using a stylet and such designs have been optimized. In an effort to address the needs of the market as related above, a through hole was drilled in the tip of this stylet driven LV lead and converted into a lead intended to be placed over a guidewire. Unfortunately, it was determined that this over-the-wire (OTW) LV lead was no longer optimum for LV placement. Problems were encountered which included jamming of the guidewire in the coil when trying to advance the lead over the guidewire or when trying to advance the guidewire through the lead. These problems were amplified when the lead was advanced through the tortuous turns of the veins of the left heart. This jamming was due in part to offsetting of the coils (causing an uneven inner diameter), coil compression, and coil elongation. As a result slidability and trackability of the lead were severely sacrificed.

To solve this jamming problem, initially, changes to the coil configuration were considered such as using a larger wire diameter, increasing the inner diameter of the coil, and decreasing the number of filars (individual wires) of the coil. Although some of these configurations were improvements over the original design, the improved results were actually very modest.

It was in light of the foregoing that the present invention was conceived and is now hereby reduced to practice.

SUMMARY OF THE INVENTION

The present invention concerns an implantable lead for electrical stimulation of the body. The implantable lead of the invention includes an elongated multi-lumen tube with a distal tip electrode having a longitudinally extending central bore. A cable conductor is received in one lumen of the multi-lumen tube for electrical connection to the distal tip electrode and an elongated polymeric tubular liner having a coefficient of friction when measured on steel in the range of 0.01 to 0.1 is received in another lumen of the multi-lumen tube generally aligned with the bore of the distal tip electrode for freely receiving a guidewire through the tubular liner and through the bore of the distal tip electrode. An electrically conductive proximal pin is attached to the multi-lumen tube distant from the distal tip electrode and, in one embodiment, the cable conductor and the proximal end of the polymeric tubular liner are attached to the proximal pin. Initially, the guidewire is implanted into the body along a desired trajectory. With the polymeric tubular liner inserted, first the distal tip electrode, then the remainder of the multi-lumen tube, are slid onto the guidewire such that the guidewire slidably advances within the polymeric tubular liner. Thereupon, the multi-lumen tube is advanced along the guidewire until a desired site is achieved and the guidewire is removed from the body and the multi-lumen tube. In another embodiment, the distal tip electrode has no central bore but the elongated polymeric tubular liner is axially aligned with the distal tip electrode for freely receiving a stylet and is attached with the distal tip electrode.

Due to the limited success achieved when changing the coil configuration and insulation as mentioned above, the present invention resulted from the investigation of an entirely new lead configuration. Instead of using a coil as a liner for guidewire passage, it was decided to investigate use of a liner composed of a suitable polymer with a low coefficient of friction such as polytetrafluoroethylene (PTFE), better known, perhaps, under the trademark TEFLON®, or equivalent. PTFE has a very low coefficient of friction, it elongates minimally under an axial load, and in tubular form has a uniform inner and outer diameter. In vitro and in vivo testing of a silicone lead with a PTFE liner has proved to be very successful. The lead does not jam on the guidewire and the lead tracks in a satisfactory manner over the guidewire through the tortuous bends of the veins of the left heart. Both in vitro and in vivo testing of a polyurethane lead with a PTFE liner have proved successful as well.

In one embodiment of a LV OTW lead with a PTFE liner, the PTFE liner is removable. In such an embodiment, the lead is successfully placed over a guidewire. Next the guidewire is removed and, finally, the PTFE liner is removed. This allows for loading of the liner with barium sulfate or bismuth subcarbonate to increase visibility of the lead under x-ray. These compounds are not commonly used in permanently implanted devices.

In another embodiment, the PTFE liner is placed in the inner diameter of a coil. This prevents the problems that were encountered, as discussed above, with the coil, yet allows for the coil to service the distal tip electrode. Furthermore, the coil increases the visibility of the lead under x-ray. In this embodiment, the PTFE liner may be removed following final placement of the lead.

In another embodiment the lead includes two cable conductors. In this embodiment, one cable conductor services the distal ring electrode (in contrast with a current design which employs tri-lumen tubing receiving two cable conductors) and the other cable conductor services the distal tip electrode. Due to the fact that the cable conductor is not coaxial with the distal tip electrode or the connector pin, a unique electrical connection is required.

Due to the fact that a PTFE liner can be of thinner wall thickness than a coil liner, the overall diameter of a lead embodying the teachings of the present invention can be decreased. This is a desirable feature, especially in the small distal and tributary veins of the left heart. Also, as a result of the smaller diameter, two leads may be placed in the larger veins of the left heart such as the coronary sinus, great cardiac vein, and posterior cardiac vein.

Another embodiment is to use the PTFE liner in a stylet placeable lead. This helps to increase trackability and steerability when placing a left sided lead that is stylet driven for those customers who prefer stylet driven left heart leads. This allows for a decreased overall diameter of right sided leads. With this construction, a smaller introducer can be used to place one lead. The same size introducer used today for placing one lead can thereby be used to place two leads, with the lead being less occlusive to the veins entering the heart.

A primary feature, then, of the present invention is the provision of an improved lead assembly for implantable medical devices providing stimulating pulses to selected body tissue.

Another feature of the present invention is the provision of such a lead assembly with an elongated polymeric liner for insertion of a guidewire for enhanced trackability and steerability of the lead.

Yet another feature of the present invention is the provision of such a lead assembly wherein the polymeric liner has a coefficient of friction in the range of 0.01 to 0.2.

Still another feature of the present invention is the provision of such a lead assembly wherein the polymeric liner is loaded with a radio opaque substance to increase lead visibility under x-ray.

Yet another feature of the present invention is the provision of such a lead assembly with a polymeric liner that can be fully removed after placement of the lead.

Still a further feature of the present invention is the provision of such a lead assembly with a polymeric liner inside the inner diameter of a conductor coil provided for electrically servicing the distal tip electrode.

Yet a further feature of the present invention is the provision of such a lead assembly with a polymeric liner that has a unique electrical connection between a non coaxial cable conductor and the distal tip electrode.

Still another feature of the present invention is the provision of such a lead assembly with a polymeric liner that has a unique electrical connection between a non coaxial cable and the proximal connector pin.

Another feature of the present invention is the provision of such a lead assembly with a polymeric liner that has a reduced diameter for optimum placement in the small distal and tributary veins of the left heart.

A further feature of the present invention is the provision of such a lead assembly with a polymeric liner that has a reduced diameter to allow for placement of more than one lead in the veins of the left heart.

Still another feature of the present invention is the provision of such a lead assembly with a polymeric liner for insertion of a stylet for enhanced trackability and steerability of the lead.

Yet another feature of the present invention is the provision of such a lead assembly with a polymeric liner for insertion of a stylet and placement in the right heart with a decreased overall diameter.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIGS. 7A, 7B, and 7C are side elevation views, in section, illustrating another embodiment of the implanted lead of the present invention and, specifically, its configuration following successive steps in it use;

FIG. 8 is a side elevation view, in section, of still another embodiment of the implanted lead embodying the present invention.

DETAILED DESCRIPTION OF THE PREFERRED EMBODIMENT

Figure 1:
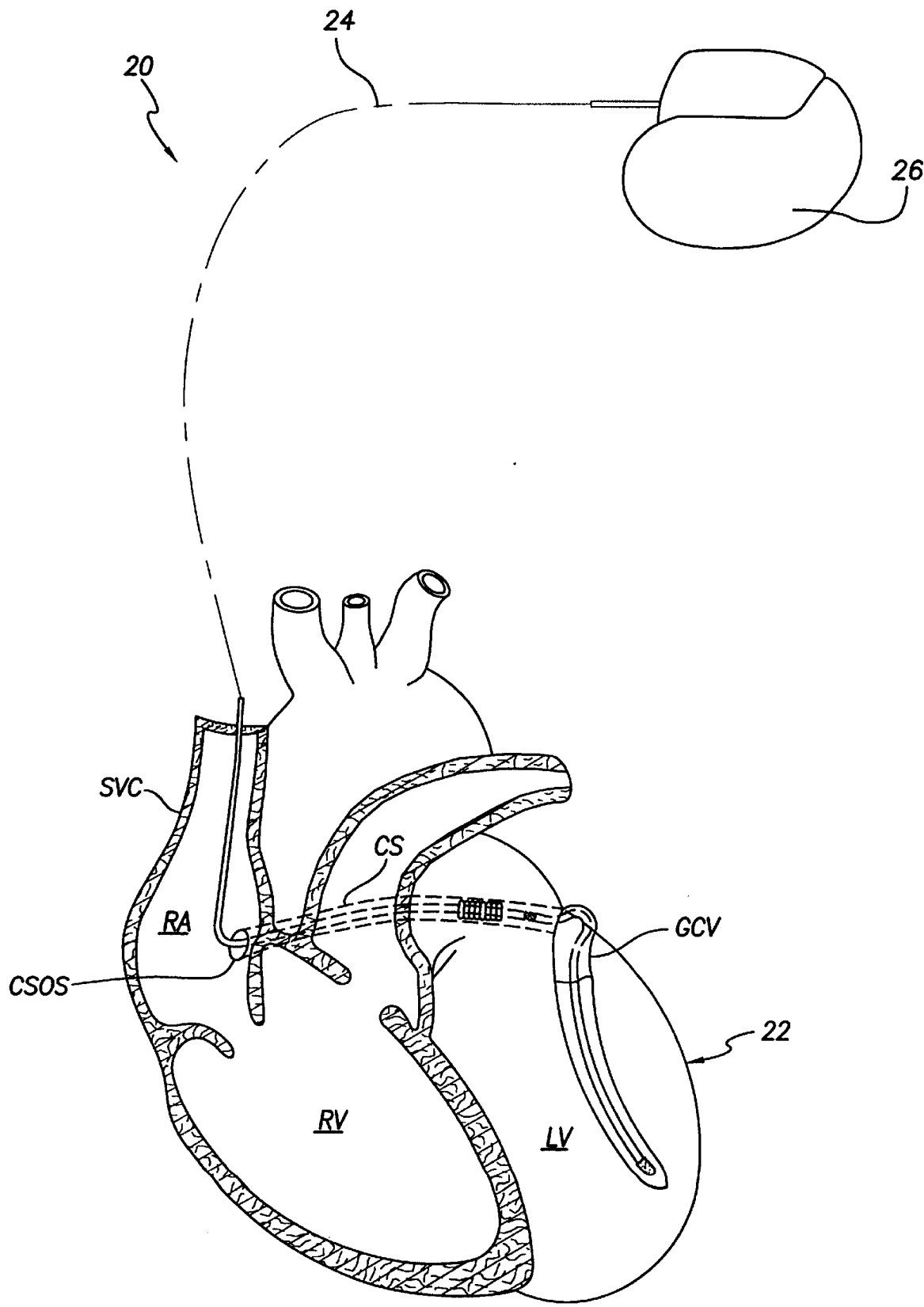
FIG. 1 illustrates an implanted system for providing electrical stimulation of a heart employing an implanted lead embodying the present invention.

In FIG. 1, there is shown a diagrammatic perspective view of an implanted system 20 for providing electrical stimulation of a heart 22 incorporating features of the present invention. Although the present invention will be described with reference to the embodiments shown in the drawings and described in the text, it should be understood that the present invention can be embodied in many alternate forms or embodiments. In addition, any suitable size, shape or type of elements or materials could be used.

In FIG. 1, there is also illustrated an implantable lead 24 embodying the invention for stimulation of the body, the heart 22 in this instance, by means of a pacemaker 26 or other suitable pulse generating device. As seen in FIG. 1, the lead 24 is inserted via the superior vena cava, SVC, into the coronary sinus ostium, CS os, located in the right atrium, RA, then advanced through the coronary sinus, CS, and placed into a tributary of the coronary sinus, preferably the great Cardiac Vein, GVC, or the left posterior cardiac vein (not shown), or other vein accessible from the coronary sinus. From this location, the lead 24 can be used to stimulate the left ventricle LV.

Figure 2:
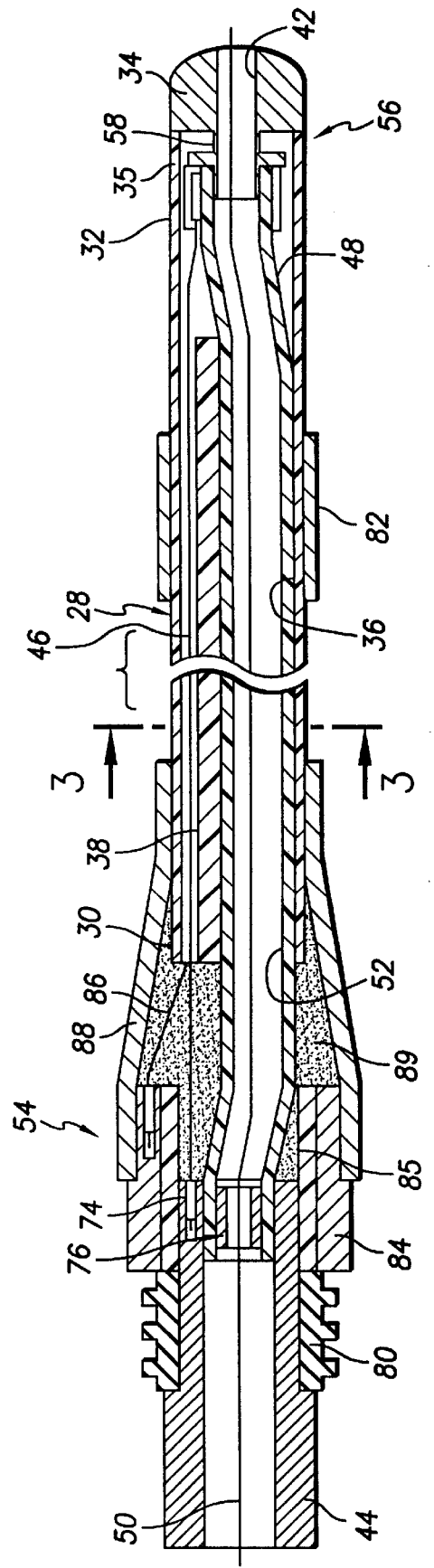
FIG. 2 is a side elevation view, in section, of one embodiment of the implanted lead embodying the present invention.
Figure 3:
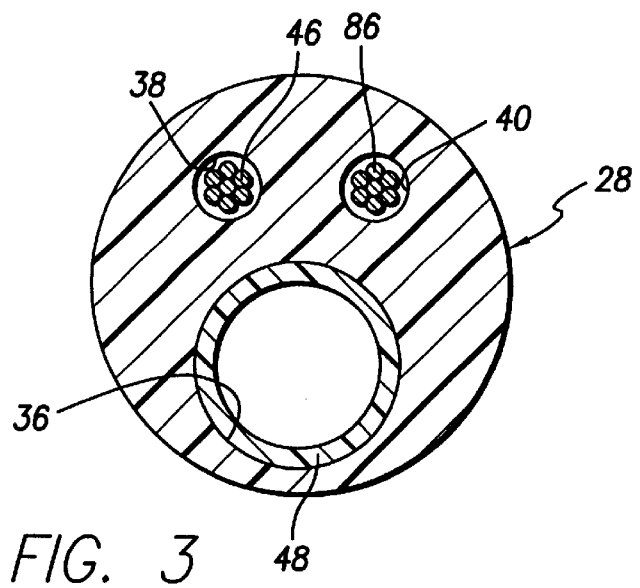
FIG. 3 is a cross-section view taken generally along the line 3—3 in FIG. 2.

As shown in FIGS. 2 and 3, the lead 24 includes an elongated multi-lumen tube 28 extending between proximal and distal ends 30, 32, respectively. A distal tip electrode 34 is suitably attached via a tubular spacer 35 to the distal end of the multi-lumen tube which, as illustrated, has a primary longitudinally extending primary lumen 36 and a pair of secondary lumina 38, 40, respectively. The tubular spacer may be bonded to the distal tip electrode with medical adhesive and may be attached to the multi-lumen tube using a butt joint. The distal tip electrode 34 itself has a longitudinally extending central bore 42 therethrough which is aligned with but longitudinally spaced from distal ends of the lumina 36, 38, and 40.

The lead 24 extends between an electrically conductive proximal pin 44 intended for connection with the pacemaker 26 and the distal tip electrode 34. A cable conductor 46 is received in the secondary lumen 38 of the multi-lumen tube 28 for electrical connection with, and extending between, the proximal pin 44 and the distal tip electrode 34.

An elongated polymeric tubular liner 48 having a coefficient of friction in the range of 0.01 to 0.20 extends between proximal and distal ends of the lead 24 and is received in the primary lumen 36 of the multi-lumen tube 28 and is generally aligned with the central bore 42 of the distal tip electrode 34. A primary function of the polymeric tubular liner 48 is to freely receive a guidewire 50 through its passageway 52 and through the central bore 42 of the distal tip electrode 34. Normally, the guidewire is first implanted along the route subsequently intended for the lead 24, then the lead is introduced onto the guidewire and advanced, or tracked, to its final position. In this instance, the low coefficient of friction of the polymeric tubular liner 48 greatly facilitates the insertion process as compared with the use of previously known lead constructions.

The liner 24, as earlier mentioned, is preferably composed of a suitable slippery polymer such as polytetrafluoroethylene (PTFE), better known, perhaps, under the trademark TEFLON®, or equivalent. PTFE has a very low coefficient of friction, it elongates minimally under an axial load, and in tubular form has a uniform inner and outer diameter. In vitro and in vivo testing of a silicone lead with a PTFE liner has proved to be very successful. The lead does not jam when using a guidewire and the lead tracks in a satisfactory manner over the guidewire through the tortuous bends of the veins of the left heart.

The proximal end of the cable conductor 46, the proximal end of the multi-lumen tubing 28, and the proximal end of the polymeric tubular liner 48 are all attached to the proximal pin 44 at a proximal connection 54. Further, the distal end of the cable conductor 46, the distal end of the multi-lumen tubing 28, and the distal end of the polymeric tubular liner 48 are all attached to the distal tip electrode 34 at a distal connection 56.

Figure 4:
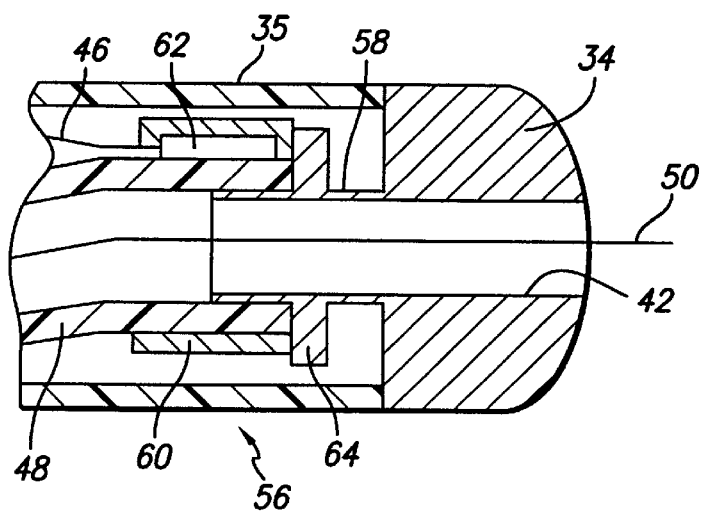
FIG. 4 is a detail cross-section view of a distal end of the implanted lead illustrated in FIG. 2.

As best illustrated in FIG. 4, the distal connection 56 includes a tubular projection 58 extending in the proximal direction, integral with the distal tip electrode 34 and coaxial with the longitudinally extending central bore 42 through the distal tip electrode. A distal crimp tube 60 is coaxial with the tubular projection 58 and, initially, is freely received over the tubular projection in a telescoping manner. The distal end of the polymeric tubular liner 48 is coaxial with the tubular projection and the distal crimp tube and is slidably received between the tubular projection and the distal crimp tube.

Figure 4A:
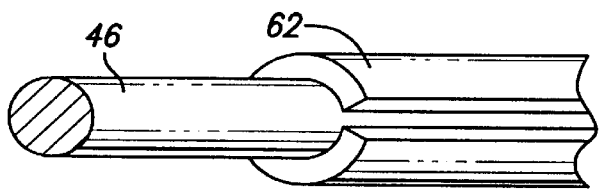
FIG. 4A is a detail perspective view of components illustrated in FIG. 4.

As seen in FIG. 4A, a distal crimp sleeve 62, which may be longitudinally split, receives the distal end of the cable conductor 46 for protective engagement of the cable conductor. The crimp sleeve 62 may first be mechanically joined to the end of the cable conductor or the crimp sleeve and cable conductor may continue to be loosely connected. In either event, the connected pair of the crimp sleeve and cable conductor are then slidably received between the tubular projection 58 and the distal end of the polymeric tubular liner 48. Thereupon, the distal connection 56 is finalized by a crimping operation which compresses the distal crimp tube 60, the distal crimp sleeve 62, and the distal end of the polymeric tubular liner 48 all into mutual engagement with the tubular projection 58. A firm unitary construction results.

Additionally, the tubular projection 58 includes an integral annular flange 64 of enlarged transverse dimension as compared with the dimension of the tubular projection. A distal end of the cable conductor is electrically connected to the annular flange as by a weld 68 such that the distal tip electrode 34 is electrically in common with the proximal pin 44.

Figure 5:
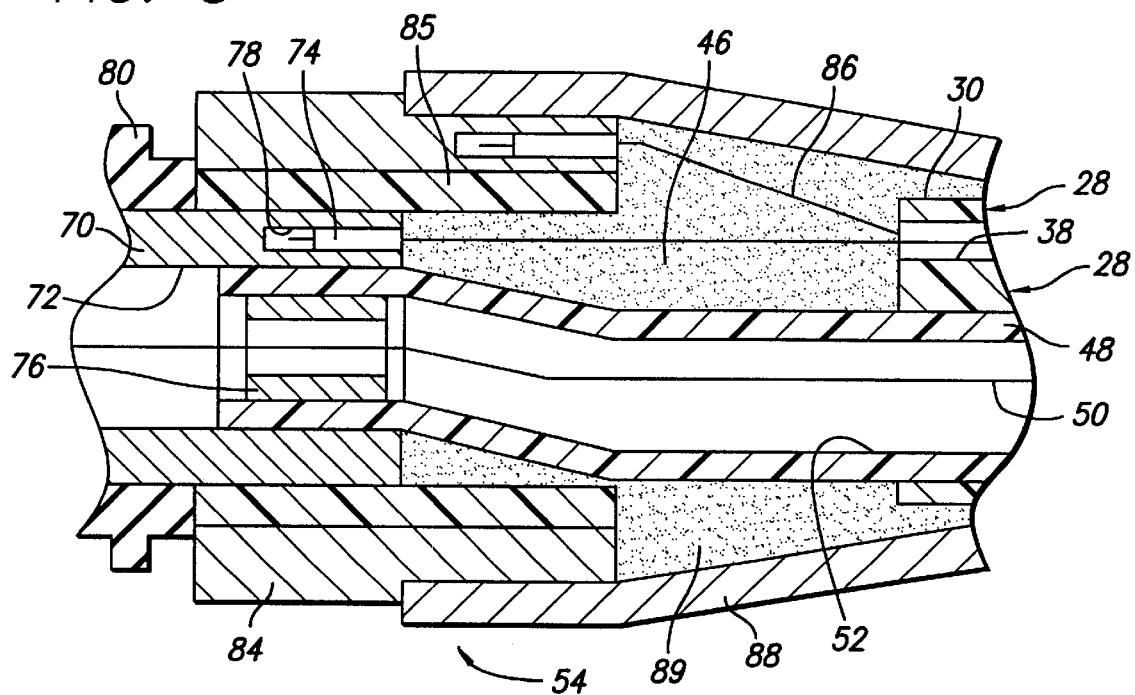
FIG. 5 is a detail cross-section view of the proximal end of the implanted lead illustrated in FIG. 2.
Figure 5A:
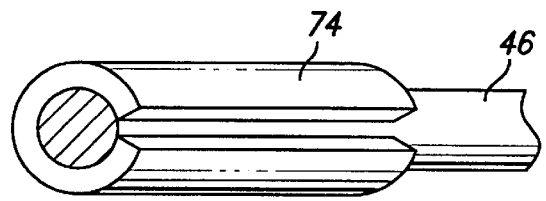
FIG. 5A is a detail perspective view of components illustrated in FIG. 5.

Turning now especially to FIG. 5, the proximal connection 54 includes a tubular projection 70 integral with the proximal pin 44, of reduced transverse dimension, and coaxial with the proximal pin extending in the direction of the distal tip electrode 34. The proximal pin 44 and the tubular projection 70 together define a coextensive conduit 72. A proximal crimp tube 74 is coaxial with the tubular projection 70 and is freely received in the conduit. Viewing FIG. 5A, a proximal crimp sleeve 74, generally similar to the distal crimp sleeve 62 and, as such, longitudinally split, receives the proximal end of the cable conductor 46 for protective engagement of the cable conductor and that combination is slidably received in a longitudinal bore 78 formed in the tubular projection 70. As with the construction of the distal connection 56, the crimp sleeve 74 may first be mechanically joined to the proximal end of the cable conductor 46 or the combination may continue to be loosely connected. In either event, the connected pair of the crimp sleeve 74 and the cable conductor 46 are then slidably received within the longitudinal bore 78. Thereupon, the proximal connection 54 is finalized by a crimping operation which compresses the proximal crimp tube 74, the proximal crimp sleeve 76, and the proximal end of the polymeric tubular liner 48 all into mutual engagement with the tubular projection 70. Again, a firm unitary construction results. When the proximal pin 44 is connected to the pacemaker 26 in the customary fashion, a suitable resilient connector seal 80 received on the tubular projection 70 serves to isolate the interior of the pacemaker from the intrusion of body fluids and the like.

As particularly well seen in FIGS. 2, 4 and 5, a distal ring electrode 82 is fittingly attached to and encompasses the multi-lumen tube 28 at a location spaced from the distal tip electrode 34. A proximal ring electrode 84 is fittingly attached to and encompasses the tubular projection 70 with an insulation band 85 interposed between the proximal ring electrode and the tubular projection for electrically isolating the two components. It was earlier mentioned that the cable conductor 46 extends between proximal and distal ends and is received in the lumen 38 for electrical connection at its proximal and distal ends, respectively, to the proximal pin 44 and to the distal tip electrode 34. In a similar manner, a second cable conductor 86 extends between proximal and distal ends and is received in the lumen 40 (FIG. 3) for electrical connection of its proximal and distal ends, respectively, to the proximal ring electrode 84 and to the distal ring electrode 82. The cable conductor 86 may be terminated to the proximal ring electrode in a manner similar to that of the cable conductor 46 to the tubular projection 70. Completing the proximal connection 54 is a flexible connector boot 88 which fittingly overlies both an end of the proximal ring electrode 84 and the proximal end of the multi-lumen tube 28. A suitable medical adhesive backfill 89 is received between the connector boot 88 and the polymeric tubular liner 48 to provide a bond between the connector proximal connector ring 84 and the multi-lumen tube although in the instance that the polymeric tubular liner 48 is removable, as will be discussed below, the medical adhesive backfill would not be employed.

Figure 6:
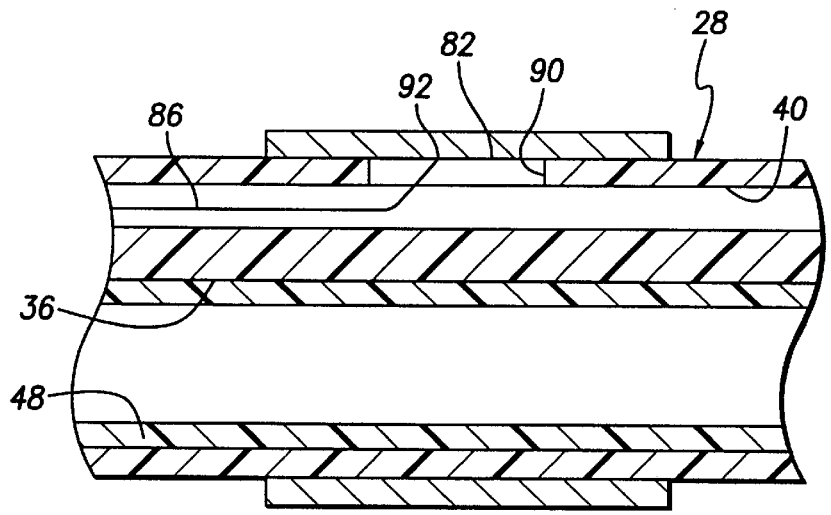
FIG. 6 is a detail cross-section view of an intermediate portion of the implanted lead illustrated in FIG. 2.

At its distal end, as seen in FIG. 6, the cable conductor 86 advances through the lumen 40, extends through an aperture 90 in the wall of the multi-lumen tube 28, and is welded as at 92 to its associated distal ring electrode 82 which overlies the aperture.

Turn now to FIGS. 7A, 7B and 7C for the description of an embodiment of an LV OTW lead with an elongated polymeric liner which is removable. In this instance, an implantable lead 94 is similar to the lead 24 except for certain modifications at the distal and proximal ends. Reference numerals will be unchanged unless there is a change in the construction of a component. As before, the distal tip electrode 34 includes a tubular projection 58 integral therewith coaxial with the central bore 42 and extending in the proximal direction. Also, the tubular projection 58 includes an integral annular flange 64 to which the distal end of the cable conductor 46 is electrically connected. At this distal end, no crimping operation is effected as earlier described. Rather, the distal end of the polymeric tubular liner 48 is fittingly, coaxially, received on the tubular projection 58. At the proximal end of the lead 94, the polymeric tubular liner 48 is slidably contained in the conduit 72 and, as at the distal end, no crimping operation is effected.

In this embodiment, viewing FIG. 7A, the lead is successfully placed over a guidewire 50. Next, viewing FIG. 7B, the guidewire 50 is removed and, finally, viewing FIG. 7C, the polymeric liner 48 is removed. This construction allows for loading of the polymer with barium sulfate or bismuth subcarbonate, compounds are not commonly used in permanent devices, to increase visibility of the lead under x-ray.

Turn now to FIG. 8 for still another embodiment of the invention. In this instance, the polymeric liner is placed in the inner diameter of a coil 96 which extends from a distal end fittingly received on the tubular projection 58 and a proximal end fittingly received on the tubular projection 70 of the proximal pin 44. This construction prevents the problems that were discussed above with the unmodified coil, yet allows for the coil to service the distal tip electrode 34. Furthermore the coil 96 increases the visibility of the lead 98 under x-ray. In this embodiment the polymeric liner 48 may be removed following final placement of the lead 98 in the body, although it may also remain in place.

Figure 9:
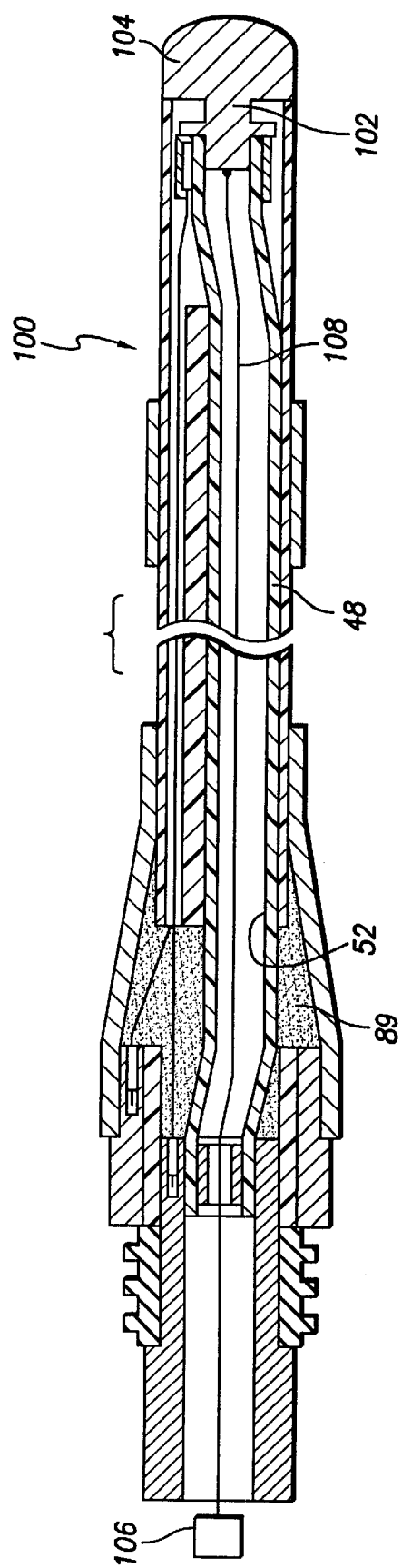
FIG. 9 is a side elevation view, in section, of yet another embodiment of the implanted lead embodying the present invention.

Turn now to FIG. 9 for yet another embodiment of the invention. In this instance, the polymeric liner 48 is employed in conjunction with a stylet placeable implantable lead 100. The distal end of the elongated polymeric tubular liner 48 is attached to a cylindrical projection 102 of a modified distal tip electrode 104 having no central bore 42 in contrast to the distal tip electrode 34 although, alternatively, it may continue to have a central bore. In this manner, the distal end of the elongated polymeric tubular liner 48 is generally aligned with the distal tip electrode 104. Thereupon, using a stylet knob 106 in a known manner, an elongated stylet 108 is inserted into, and advanced in slidable engagement with, the passageway 52 of the polymeric tubular liner. Then, using the stylet 106, the lead 100 is advanced into the body along the desired trajectory until a desired site is achieved. Thereafter, the stylet is detached from the distal tip electrode and removed from the lead and, if desired, the polymeric tubular liner may also be removed from the lead.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable lead for electrical stimulation of the body comprising:

an elongated multi-lumen tube extending between proximal and distal ends;

a distal tip electrode attached to the distal end of the multi-lumen tube and having a longitudinally extending central bore therethrough;

a cable conductor received in one lumen of the multi-lumen tube for electrical connection to the tip electrode;

an elongated polymeric tubular liner having a coefficient of friction in the range of 0.01 to 0.20 extending between proximal and distal ends and received in another lumen of the multi-lumen tube generally aligned with the bore of the distal tip electrode for freely receiving a guidewire through the tubular liner and through the bore of the distal tip electrode;

an electrically conductive proximal pin distant from the tip electrode; wherein the proximal end of the first cable conductor, the proximal end of the multi-lumen tubing, and the proximal end of the polymeric tubular liner are all attached to the proximal pin at a generally proximal connection;

wherein the distal end of the first cable conductor, the distal end of the multi-lumen tubing, and the distal end of the polymeric tubular liner are all attached to the tip electrode at a generally distal connection;

wherein the distal connection includes:

a tubular projection integral with the tip electrode and coaxial with the longitudinally extending central bore therethrough and extending in the proximal direction;

a distal crimp tube coaxial with the tubular projection of the tip electrode and freely received thereover;

wherein the distal end of the polymeric tubular liner is coaxial with the tubular projection and the distal crimp tube and slidably received between the tubular projection and the distal crimp tube;

a distal crimp sleeve receiving the distal end of the cable conductor for protective engagement thereof slidably received between the tubular projection and the distal end of the polymeric tubular liner; and the distal connection being coupled by a crimping operation which compresses the distal crimp tube, the distal crimp sleeve, and the distal end of the polymeric tubular liner all into mutual engagement with the tubular projection.

2. The implantable lead, as set forth in claim 1, comprising:

an electrically conductive proximal pin distant from the tip electrode, wherein the cable conductor and the proximal end of the polymeric tubular liner are attached to the proximal pin.

3. The implantable lead, as set forth in claim 1, wherein:

the tubular projection has an integral annular flange; and a distal end of the cable conductor is electrically connected to the annular flange;

whereby the tip electrode is electrically in common with the proximal pin.

4. The implantable lead, as set forth in claim 1, wherein the proximal connection includes:

a tubular projection integral with the proximal pin and coaxial therewith extending in the direction of the distal tip electrode, the proximal pin and the tubular projection together defining a conduit-therethrough;

a proximal crimp tube coaxial with the tubular projection and freely received in the conduit;

wherein the proximal end of the polymeric tubular liner is coaxial with the proximal pin and the proximal crimp tube and slidably received between the tubular projection and the crimp tube;

a proximal crimp sleeve receiving the proximal end of the cable conductor for protective engagement thereof slidably received between the tubular projection and the proximal end of the polymeric tubular liner; and the proximal connection being finalized by a crimping operation which compresses the tubular projection, the proximal crimp tube, the proximal crimp sleeve, and the proximal end of the polymeric tubular liner all into mutual engagement.

5. The implantable lead, as set forth in claim 1, comprising:

an electrically conductive proximal pin distant from the tip electrode;

a distal ring electrode attached to and encompassing the multi-lumen tube at a location spaced from the distal tip electrode;

a proximal ring electrode attached to and encompassing the multi-lumen tube at a location spaced from the proximal pin;

wherein the elongated multi-lumen tube has first, second, and third independent longitudinally extending lumina;

wherein the cable conductor extends between proximal and distal ends and is received in the first lumen for electrical connection at its proximal and distal ends, respectively, to the proximal pin and to the distal tip electrode; and wherein a second cable conductor extends between proximal and distal ends and is received in the second lumen for electrical connection to its proximal and distal ends, respectively, to the proximal ring electrode and to the distal ring electrode.

6. An implantable lead for electrical stimulation of the body comprising:

an elongated multi-lumen tube extending between proximal and distal ends;

a distal tip electrode attached to the distal end of the multi-lumen tube and having a longitudinally extending central bore therethrough;

a cable conductor received in one lumen of the multi-lumen tube for electrical connection to the tip electrode;

an elongated polymeric tubular liner having a coefficient of friction in the range of 0.01 to 0.20 extending between proximal and distal ends and received in another lumen of the multi-lumen tube generally aligned with the bore of the distal tip electrode for freely receiving a guidewire through the tubular liner and through the bore of the distal tip electrode;

wherein:

the distal tip electrode includes a tubular projection integral therewith, coaxial with the central bore of the distal tip electrode and extending in the proximal direction; and the distal end of the polymeric tubular liner is fittingly received on the tubular projection so as to be coaxial therewith.

7. The implantable lead, as set forth in claim 6, wherein:

the tubular projection includes an integral annular flange; and the distal end of the first cable conductor is electrically connected to the annular flange.

8. An implantable lead for electrical stimulation of the body comprising:

an elongated multi-lumen tube extending between proximal and distal ends;

a distal tip electrode attached to the distal end of the multi-lumen tube and having a longitudinally extending central bore therethrough;

a cable conductor received in one lumen of the multi-lumen tube for electrical connection to the tip electrode;

an elongated polymeric tubular liner having a coefficient of friction in the range of 0.01 to 0.20 extending between proximal and distal ends and received in another lumen of the multi-lumen tube generally aligned with the bore of the distal tip electrode for freely receiving a guidewire through the tubular liner and through the bore of the distal tip electrode;

wherein:

the proximal pin includes a tubular projection integral with the proximal pin and coaxial therewith extending in the distal direction, the proximal pin and the tubular projection together defining a conduit therethrough, wherein the distal tip electrode includes a tubular projection integral therewith, coaxial with the central bore of the distal tip electrode and extending in the proximal direction; and further comprising a coiled cable conductor extending between a proximal end electrically connected with the tubular projection of the proximal pin and a distal end electrically connected with the tubular projection of the distal tip electrode; and wherein the polymeric tubular liner is freely received through the conduit and in a coaxial relationship with the coiled cable and extending continuously between proximal pin and the distal tip electrode.

* * * * *